United States Patent
Chen et al.

(10) Patent No.: US 11,647,889 B2
(45) Date of Patent: May 16, 2023

(54) NEAR-INFRARED FLUORESCENCE IMAGING FOR BLOOD FLOW AND PERFUSION VISUALIZATION AND RELATED SYSTEMS AND COMPUTER PROGRAM PRODUCTS

(71) Applicant: East Carolina University, Greenville, NC (US)

(72) Inventors: Cheng Chen, Greenville, NC (US); Jiahong Jin, Greenville, NC (US); Thomas Bruce Ferguson, Raleigh, NC (US); Kenneth Michael Jacobs, Greenville, NC (US); Taylor Forbes, Greenville, NC (US); Bryent Tucker, Rocky Mount, NC (US); Xin Hua Hu, Greenville, NC (US)

(73) Assignee: East Carolina University, Greenville, NC (US)

( * ) Notice: Subject to any disclaimer, the term of this patent is extended or adjusted under 35 U.S.C. 154(b) by 398 days.

(21) Appl. No.: 16/829,468

(22) Filed: Mar. 25, 2020

(65) Prior Publication Data

US 2020/0305721 A1    Oct. 1, 2020

Related U.S. Application Data

(60) Provisional application No. 62/823,715, filed on Mar. 26, 2019.

(51) Int. Cl.
*A61B 1/00* (2006.01)
*A61B 5/00* (2006.01)
(Continued)

(52) U.S. Cl.
CPC .. *A61B 1/000094* (2022.02); *A61B 1/000095* (2022.02); *A61B 1/0638* (2013.01);
(Continued)

(58) Field of Classification Search
CPC ... A61B 5/0071; A61B 5/0077; A61B 5/7217; A61B 1/000095; A61B 1/000094;
(Continued)

(56) References Cited

U.S. PATENT DOCUMENTS

| 8,644,911 B1 | 2/2014 | Panasyuk |
| 9,226,673 B2 | 1/2016 | Ferguson, Jr. et al. |

(Continued)

FOREIGN PATENT DOCUMENTS

| CA | 2658811 A1 | 2/2007 |
| JP | 2017136182 A | 8/2017 |

(Continued)

OTHER PUBLICATIONS

Communication pursuant to Article 94(3) EPC, EP 19 737 931.6, dated Apr. 21, 2022, 5 pages.
(Continued)

*Primary Examiner* — John R Schnurr
(74) *Attorney, Agent, or Firm* — Stanek Lemon Crouse & Meeks, PA

(57) ABSTRACT

Systems for obtaining an image of a target are provided including at least one multi-wavelength illumination module configured to illuminate a target using two or more different wavelengths, each penetrating the target at different depths; a multi-wavelength camera configured to detect the two or more different wavelengths illuminating the target on corresponding different channels and acquire corresponding images of the target based on the detected two or more different wavelengths illuminating the target; a control module configured synchronize illumination of the target by the at least one multi-wavelength illumination module and detection of the two or more different wavelengths by the camera; an analysis module configured to receive the acquired images of the target and analyze the acquired (Continued)

images to provide analysis results; and an image visualization module modify the acquired images based on the analysis results to provide a final improved image in real-time.

18 Claims, 8 Drawing Sheets

(51) Int. Cl.
    *G01N 21/64*     (2006.01)
    *G06T 5/00*     (2006.01)
    *A61B 5/026*     (2006.01)
    *A61B 1/06*     (2006.01)

(52) U.S. Cl.
    CPC .......... *A61B 5/0071* (2013.01); *A61B 5/0077* (2013.01); *A61B 5/0261* (2013.01); *A61B 5/7217* (2013.01); *G01N 21/6456* (2013.01); *G01N 21/6486* (2013.01); *G06T 5/002* (2013.01); *A61B 5/7203* (2013.01); *G06T 2207/10064* (2013.01); *G06T 2207/10152* (2013.01); *G06T 2207/30104* (2013.01)

(58) Field of Classification Search
    CPC ... A61B 5/7203; A61B 1/0638; A61B 5/0261; G01N 21/6456; G01N 21/6486; G06T 5/002; G06T 2207/10064; G06T 2207/10152; G06T 2207/30104
    See application file for complete search history.

(56) References Cited

U.S. PATENT DOCUMENTS

| | | | |
|---|---|---|---|
| 9,271,658 B2 | 3/2016 | Ferguson, Jr. et al. | |
| 9,480,424 B2 | 11/2016 | Darty et al. | |
| 10,058,256 B2 | 8/2018 | Chen et al. | |
| 10,205,892 B2 | 2/2019 | Darty et al. | |
| 10,390,718 B2 | 8/2019 | Chen et al. | |
| 2003/0158470 A1 | 8/2003 | Wolters | |
| 2011/0090325 A1 | 4/2011 | Hauger et al. | |
| 2012/0277559 A1 | 11/2012 | Kohl-Bareis | |
| 2013/0012794 A1 | 1/2013 | Zeng | |
| 2015/0044098 A1 | 2/2015 | Smart et al. | |
| 2015/0078642 A1 | 3/2015 | Fang | |
| 2015/0282749 A1 | 10/2015 | Zand et al. | |
| 2016/0022181 A1 | 1/2016 | Valsan et al. | |
| 2016/0345835 A1 | 12/2016 | Darty | |
| 2017/0198349 A1 | 7/2017 | Rice | |
| 2017/0236281 A1 | 8/2017 | Dacosta | |
| 2017/0274205 A1* | 9/2017 | Chen | A61N 1/08 |
| 2017/0278238 A1 | 9/2017 | Noji | |
| 2018/0020932 A1* | 1/2018 | Chen | A61B 1/044 600/479 |
| 2018/0092699 A1 | 4/2018 | Finley | |
| 2018/0153422 A1 | 6/2018 | Watanabe | |
| 2018/0234603 A1* | 8/2018 | Moore | H04N 5/2352 |
| 2019/0009387 A1 | 1/2019 | Rodriguez et al. | |
| 2019/0079011 A1* | 3/2019 | Frangioni | G01N 21/6456 |
| 2020/0271583 A1* | 8/2020 | Ortiz Egea | G01J 3/12 |

FOREIGN PATENT DOCUMENTS

| | | |
|---|---|---|
| JP | 2017534378 A | 11/2017 |
| WO | WO 2007/136880 A2 | 11/2007 |
| WO | WO 2016/153741 A1 | 9/2016 |

OTHER PUBLICATIONS

HyperView™, HyperMed Medical Spectral Imaging, 2017, 5 pages.
A. A. Kamshilin, M. A. Volynsky, O. Khayrutdinova, D. Nurkhametova, L. Babayan, A. V. Amelin, O. V. Mamontov, and R. Giniatullin, "Novel capsaicin-induced parameters of microcirculation in migraine patients revealed by imaging photoplethysmography," The journal of headache and pain 19, 43 (2018).
A. Jubran, "Pulse oximetry," Critical care 19, 272 (2015).
A. Nouvong, B. Hoogwerf, E. Mohler, B. Davis, A. Tajaddini, and E. Medenilla, "Evaluation of Diabetic Foot Ulcer Healing With Hyperspecfral Imaging of Oxyhemoglobin and Deoxyhemoglobin," Diabetes Care 32, 2056-2061 (2009).
Akobeng AK. Understanding diagnostic tests 3: Receiver operating characteristic curves. Acta Paediatr 2007; 96: 644-6screening47.
Alahdab F, Wang AT, Elraiyah TA, Malgor RD, Rizvi AZ, Lane MA, Prokop LJ, Montori VM, Conte MS, Murad MH. A systematic review for the screening for peripheral arterial disease in asymptomatic patients, J Vasc Surg 2015; 61: 42S-53S.
Bornstein JE, Munger JA, Deliz JR, Mui A, Cheng C, Kim S, Khaitov S, Chessin DB, Ferguson TB, Bauer JJ. Assessment of bowel end perfusion after mesenteric division: eye vs. SPY. 2018. J Surg Res 230:179-185.
Briers D DD, Hirst E, Kirkpatrick SJ, Larsson M, Steenbergen W, Stromberg T, Thompson OB. Laser speckle contrast imaging: Theoretical and practical limitations. Journal of biomedical optics 2013; 18: 066018.
C. Chen, J. Q. Lu, K. Li, S. Zhao, R. S. Brock, and X. H. Hu, "Numerical study of reflectance imaging using a parallel Monte Carlo method" Med. Phys. 34, 2939-2948 (2007).
Carreau A, El Hafny-Rahbi B, Matejuk A, Grillon C, Kieda C. Why is the partial oxygen pressure of human tissues a crucial parameter? Small molecules and hypoxia. J Cell Mol Med 2011; 15: 1239-1253
Collins JA, Rudenski A, Gibson J, Howard L, O'Driscoll R. Relating oxygen partial pressure, saturation and content: The haemoglobin-oxygen dissociation curve. Breathe (Sheff) 2015; 11: 194-201.
Criqui MH, Aboyans V. Epidemiology of peripheral artery disease. Circulation research 2015; 116: 1509-1526.
D. Alvarez, R. Hornero, J. V. Marcos, and F. d. Campo, "Multivariate Analysis of Blood Oxygen Saturation Recordings in Obstructive Sleep Apnea Diagnosis," IEEE Transactions on Biomedical Engineering 57, 2816-2824 (2010).
Davies JL CC, Piek JJ. Coronary physiological parameters at a crossroads. Eurointervention : journal of EuroPCR in collaboration with the Working Group on Interventional Cardiology of the European Society of Cardiology 2017; 13: 1-4.
De Bruyne B, Pijls NH, Kalesan B, Barbato E, Tonino PA, Piroth Z, Jagic N, Mobius-Winkler S, Rioufol G, Witt N, Kale P, Mac-Carthy P, Engstrom T, Oldroyd KG, Mavromatis K, Manoharan G, Verlee P, Frobert O, Curzen N, Johnson JB, Juni P, Fearon WF. Fractional flow reserve-guided pci versus medical therapy in stable coronary disease. N. Engl J Med 2012; 367: 991-1001.
Ferguson TB Jr BA. Improving the quality and outcomes of coronary artery bypass grafting procedures. Expert Review of Cardiovascular Therapy 2016; 14: 617-631.
Ferguson TB Jr CC, Kim S, Jacobs K, Zeng Z, Zhu Z, Buch A, Basham J. Noninvasive quantification of blood flow in epicardial coronary arteries, coronary artery bypass grafts, and anastomoses. Innovations 2017; 12: 50-59.
Ferguson TB, Jr., Chen C, Babb JD, Efird JT, Daggubati R, Cahill JM. Fractional flow reserve-guided coronary artery bypass grafting: Can intraoperative physiologic imaging guide decision making? J Thorac Cardiovasc Surg 2013; 146: 824-835 e821.
Force USPST, Curry SJ, Krist AH, Owens DK, Barry MJ, Caughey AB, Davidson KW, Doubeni CA, Epling JW, Jr., Kemper AR, Kubik M, Landefeld CS, Mangione CM, Silverstein M, Simon MA, Tseng CW, Wong JB. Screening for peripheral artery disease and cardiovascular disease risk assessment with the ankle-brachial index: US preventive services task force recommendation statement. JAMA 2018; 320: 177-183.
Fowkes FG MG, Butcher I, et al. Ankle Brachial Index Collaboration. Ankle brachial index combined with framingham risk score to predict cardiovascular events and mortality. JAMA 2008; 300: 197-2008.
Fowkes FGR, Rudan D, Rudan I, Aboyans V, Denenberg JO, McDermott MM, Norman PE, Sampson UKA, Williams LJ, Mensah GA, Criqui MH. Comparison of global estimates of prevalence and

(56) References Cited

OTHER PUBLICATIONS risk factors for peripheral artery disease in 2000 and 2010: A systematic review and analysis. The Lancet 2013; 382: 1329-1340.
G. C. Gurtner, G. E. Jones, P. C. Neligan, M. I. Newman, B. T. Phillips, J. M. Sacks, and M. R. Zenn, "Intraoperative laser angiography using the SPY system: review of the literature and recommendations for use," Annals of Surgical Innovation and Research 7, 1 (2013.)
Gerhard-Herman MD, Gornik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, Treat-Jacobson D, Walsh ME. 2016 aha/acc guideline on the management of patients with lower extremity peripheral artery disease: A report of the american college of cardiology/american heart association task force on clinical practice guidelines. Circulation 2017; 135: e726-e779.
Gerhard-Herman MD, Gornik HL, Barrett C, Barshes NR, Corriere MA, Drachman DE, Fleisher LA, Fowkes FG, Hamburg NM, Kinlay S, Lookstein R, Misra S, Mureebe L, Olin JW, Patel RA, Regensteiner JG, Schanzer A, Shishehbor MH, Stewart KJ, Treat-Jacobson D, Walsh ME. 2016 aha/acc guideline on the management of patients with lower extremity peripheral artery disease: Executive summary: A report of the american college of cardiology/american heart association task force on clinical practice guidelines. Circulation 2017; 135: e686-e725.
Gomaa D, Rodriquez D, Jr., Petro M, Blakeman TC, Branson RD. Impact of oxygenation status on the noninvasive measurement of hemoglobin. Mil Med 2017; 182: 87-91.
Guirguis-Blake JM, Evans CV, Redmond N, Lin JS. Screening for peripheral artery disease using the ankle-brachial index: Updated evidence report and systematic review for the us preventive services task force. JAMA 2018; 320: 184-196.
Hlatky MA, De Bruyne B, Pontine G, Patel MR, Norgaard BL, Byrne RA, Curzen N, Purcell I, Gutberiet M, Rioufol G, Hink U, Schuchlenz HW, Feuchtner G, Gilard M, Andreini D, Jensen JM, Hadamitzky M, Wilk A, Wang F, Rogers C, Douglas PS, Investigators P. Quality of life and economic outcomes of assessing fractional flow reserve with computed tomography angiography: The platform study. J Am Coll Cardiol 2015, 10.1016/j.jacc.2015. 09.051.
J. Allen, "Photoplethysmography and its application in clinical physiological measurement," Physiological Measurement 28, R1-R39 (2007).
J. Q. Lu, C. Chen, D. W. Pravica, R. S. Brock, and X. H. Hu, "Validity of a closed-form diffusion solution in P1 approximation for reflectance imaging with an oblique beam of arbitrary profile," Med. Phys. 35, 3979-3987 (2008).
Jelani QU, Petrov M, Martinez SC, Holmvang L, Al-Shaibi K, Alasnag M. Peripheral arterial disease in women: An overview of risk factor profile, clinical features, and outcomes, Curr Atheroscler Rep 2018; 20: 40.
Khan TH FF, Niazi K, Critical review of the ankle brachial index. Current Cardiology Reviews 2008; 4: 101-106.
Kim SK HL, McNames J. Tracking of rhythmical biomedical signals using the maxima a posteriori adaptive marginalized particle filter. British Journal of Health Informatics and Monitoring 2015; 2.
L Higgins G. What is the potential for false positive results in ankle brachial index measurements performed by emergency providers? Journal of General Practice 2013; 01.
Leach RM, Treacher DF. Oxygen transport: 2: Tissue hypoxia. BMJ 1998; 317(7169):1370-1373.
Lijmer JG HM, van den Dungen JJAM, Loonstra J, Smit AJ. Roc analyses of non-invasive tests for peripheral arterial disease. Ultrasound in Med and Biol 1996; 22: 391-398.
Loong T-W. Clinical review: Understanding sensitivity and specificity with the right side of the brain. BMJ 2003: 327: 716-719.
M. R. Future, "Perfusion Imaging Market Research Report—Global Forecast till 2024," (WantStats Research and Media Pvt Ltd. 2019).
Macintyre NR. Tissue hypoxia: implications for the respiratory clinician. Respiratory Care 2014. 59(10):1590-1596.

Martin DS, Khosravi M, Grocott M, Mythen MG. Concepts in hypoxia reborn. Crit Care 2010; 14(4):315.
McDermott M, Criqui MH. Ankle-brachial index screening and improving peripheral artery disease detection and outcomes. JAMA 2018; 320: 143-145.
McDermott MM. Lower extremity manifestations of peripheral artery disease: The pathophysiologic and functional impiications of leg ischemia. Circulation research 2015; 116: 1540-1550.
Michiels C. Physiological and Pathological Responses to Hypoxia. Am J Physiol 2004; 164(6):1875-1882.
Notification of Transmittal of the International Search Report and the Written Opinion of the International Searching Authority, or the Declaration, PCT/US2019/035792, dated Sep. 10, 2019, 11 pages.
P. Tian, C. Chen, J. Jin, H. Hong, J. Q. Lu, and X.-H. Hu, "Quantitative characterization of turbidity by radiative transfer based reflectance imaging," Biomed. Opt. Express 9, 2081-2094 (2018).
P. Tian, X. Chen, J. Jin, J. Q. Lu, X. Liang, and X. H. Hu, "A stochastic model for quantifying effect of surface roughness on light reflection by diffuse reflectance standards." Opt. Eng. 57 (in press) (2018).
Pijls NHJ. Fractional flow reserve to guide coronary revascularization. Circulation Journal 2013; 77: 561-569.
R. Bi, J. Dong, C. L. Poh, and K. Lee, "Optical methods for blood perfusion measurement: theoretical comparison among four different modalities," J. Opt. Soc. Am. A 32, 860-866 (2015).
S. CN, Han SH, Lim SH, Hong YS, Won JH, Bee JI, Jo J. Factors affecting the validity of ankle-brachial index in the diagnosis of peripheral arterial obstructive disease. Angiology 2010; 61: 392-396.
Semenza GL. Vascular Responses to Hypoxia and Ischemia. Arterioscler Thromb Vasc Dial 2010. Apr.: 30(4):648-652.
Thabane L ML, Zhang S, Samaan Z, Marcucci M, Ye C, Thabane M, Giangregorio L, Dennis B, Kosa D, Debono VB, Dillenburg R, Fruci V, Bawor M, Lee J, Wells G, Goldsmith CH. A tutorial on sensitivity analyses in clinical trials: The what, why, when and how. BMC Medical Research Methodology 2013; 13: 1-12.
Tonino PAL dBB, Pijls NHJ, Siebert U, Ikeno F, van't Veer M, Knauss V, Manoharan G, Engstrom T, Oldroyd KG, Ver Lee PN, MacCarthy PA, Fearon WA, for the FAME Study Investigators. Fractional flow reserve versus angiography for guiding percutaneous coronary intervention. N. Engl J Med 2009; 360: 213-224.
Vaz PG, Humeau-Heurtier A, Figueiras E, Correia C, Cardoso J. Laser speckle imaging to monitor microvascular blood flow: A review. IEEE Rev Biomed Eng 2016; 9: 106-120.
White CJ. Cookbook medicine is the recipe for successfully managing patients with pad. J Am Coll Cardiol 2018; 72: 1012-1014.
Wikstrom J HT, Johansson L, Lind L, Ahlstrom H. Ankle brachial index < 0.9 underestimates the prevalence of peripheral artery occlusive disease assessed with whole-bodu magnetic resonance angiograghy in the elderly. Acta Radialogica 2008; 49: 143-149.
Wikstrom J, Hansen T, Johansson L, Ahlstrom H, Lind L. Lower extremity artery stenosis distribution in an unselected elderly population and its relation to a reduced ankle-brachial index. J Vasc Surg 2009; 50: 330-334.
X. Chen, Y. Feng, J. Q. Lu, X. Liang, J. Ding, Y. Du, and X. H. Hu, "Fast method for inverse determination of optical parameters from two measured signals," Optics letters 38, 2095-2097 (2013).
Y. An, Y. Kang, J. Lee, C. Ahn, K. Kwon and C. Choi, "Blood flow characteristics of diabetic patients with complications detected by optical measurement," BioMedical Engineering OnLine 17, 25 (2018).
Y. Sun, and N. Thakor, "Photoplethysmography Revisited: From Contact to Noncontact, From Point to Imaging," IEEE Trans Biomed. Eng. 63, 463-477 (2016).
International Search Report, PCT/US2020/024645, dated Sep. 2, 2020, 9 pages.
Tian et al., "Quantitative characterization of turbidity by radiative transfer based reflectance imaging," Biomedical Optics Express, vol. 9, No. 5, pp. 2018-2094, Apr. 4, 2018.
Radrich et al., "Quantitative multi-spectral oxygen saturation measurements independent of tissue optical properties," Journal of Biophotonics, pp. 83-99, Jan. 1, 2016.

(56) References Cited

OTHER PUBLICATIONS

International Search Report and Written Opinion, PCT/US2020/022295, dated Jun. 30, 2020, 12 pages.
International Search Report and Written Opinion, PCT/US2019/049489, dated Jun. 3, 2020.

\* cited by examiner

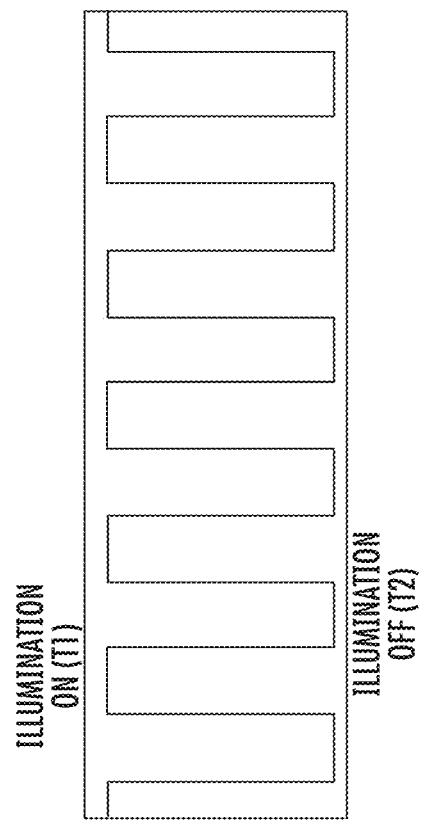
FIG. 2
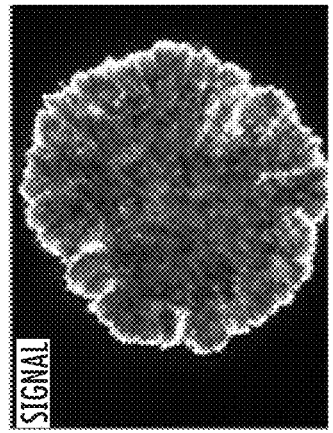
FIG. 3C
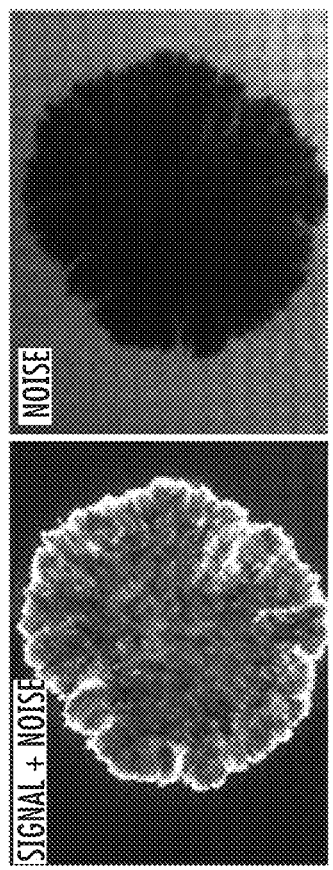
FIG. 3B
FIG. 3A

INITIAL ICG PROTOTYPE - FA 1ST TEST (0.5CC ICG DYE) - SINGLE WAVELENGTH

BACKGROUND REMOVED

F# = 1.4, 400mW PULSING LASER.

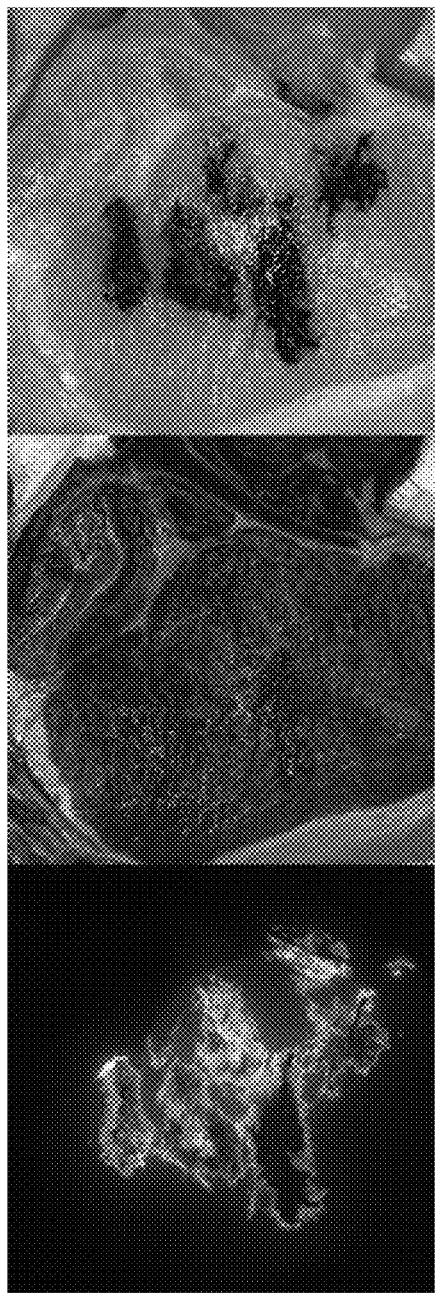
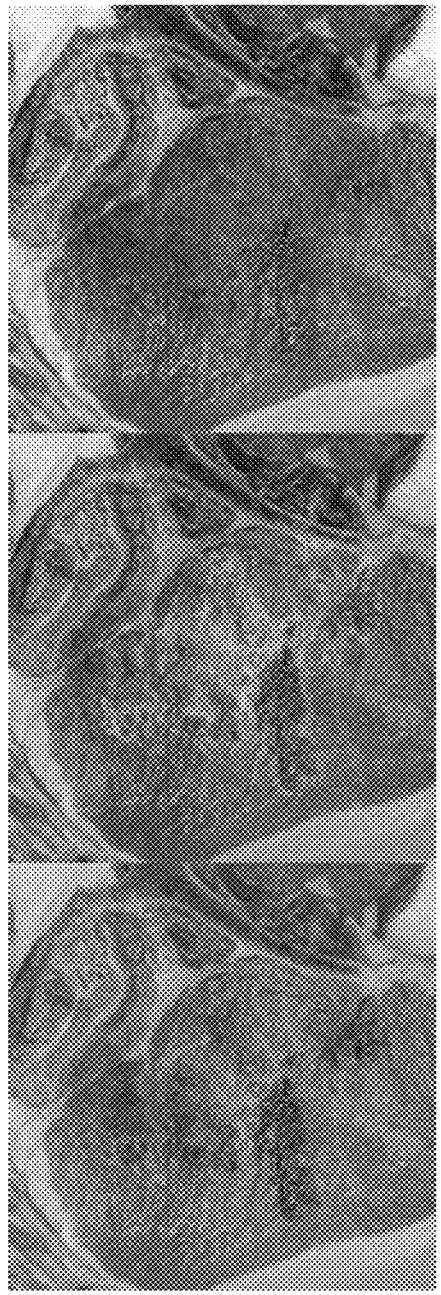
FIG. 9A  FIG. 9B  FIG. 9C  FIG. 9D  FIG. 9E  FIG. 9F

NEAR-INFRARED FLUORESCENCE IMAGING FOR BLOOD FLOW AND PERFUSION VISUALIZATION AND RELATED SYSTEMS AND COMPUTER PROGRAM PRODUCTS

CLAIM OF PRIORITY

The present application claims priority to U.S. Provisional Application Ser. No. 62/823,715 filed on Mar. 26, 2019 entitled NEAR-INFRARED FLUORESCENCE IMAGING FOR BLOOD FLOW AND PERFUSION VISUALIZATION AND RELATED METHODS AND SYSTEMS, the contents of which are hereby incorporated herein by reference as if set forth in its entirety.

FIELD

The present inventive concept relates generally to blood flow and perfusion and, in particular, to blood flow and perfusion depiction, analysis, quantification and visualization using imaging techniques, such as fluorescence imaging.

BACKGROUND

Fluorescence imaging generally involves injection of a fluorophobe into the blood stream. This fluorophobe is stimulated to fluoresce by illumination with an excitation light of specific wavelength. The lower-energy fluorescence pattern in vessels and tissues is captured by imaging at a different wavelength than the excitation wavelength.

The illumination sources of current near-infrared fluorescence devices using fluorophobes, for example, indocyanine green dye (ICG) for clinical application are typically light emitting diodes (LEDs), Halogen bulbs or lasers with typical illumination intensities of greater than 10 mW/cm$^2$. Conventional systems generally provide this illumination from a single source. There are several consequences that result from this design.

Because the fluorescence emission light energy is generally very weak, imaging results (fluorescence intensity in blood and/or tissues) can be affected by the excitation light, and by the presence of ambient light also illuminating the field of view (FOV). Most of the commercial devices use high power illumination and optical filtering mechanisms to separate the fluorescence emission signal from excitation/ambient signal to increase signal to noise ratio. However, this design may not be satisfactory when the ambient light is present in the FOV. In practice, most of the current devices require that ambient light, such as the overhead room light, surgical light, head light and the like, to be turned off for imaging, which can be inconvenient or even disruptive during procedures.

Furthermore, the depth of detection relative to the surface of tissues being imaged in current fluorescence technology design is not able to be determined and, therefore, may not be controllable. This is a result of the fact that current device designs generally either use a single wavelength laser that only allows a certain depth of penetration, or a broad band LED or Halogen illumination that leads to a heterogeneous, but un-definable depth of penetration.

SUMMARY

Some embodiments of the present inventive concept provide systems for obtaining an image of a target. The system includes at least one multi-wavelength illumination module configured to illuminate a target using two or more different wavelengths, each of the two or more different wavelengths penetrating the target at different depths; a multi-wavelength camera configured to detect the two or more different wavelengths illuminating the target on corresponding different channels and acquire corresponding images of the target based on the detected two or more different wavelengths illuminating the target; a control module configured synchronize illumination of the target by the at least one multi-wavelength illumination module and detection of the two or more different wavelengths by the camera; an analysis module configured to receive the acquired images of the target associated with each of the two or more wavelengths and analyze the acquired images to provide analysis results; and an image visualization module configured to receive the analysis results and modify the acquired images based on the analysis results to provide a final improved image in real-time, the final improved images having reduced ambient light noise.

In further embodiments, the image visualization module may be configured to modify the image by performing multi-spectral image combinations, image enhancements, contrast and brightness adjustment and overlay procedures to provide the final improved image in real-time.

In still further embodiments, the multi-spectral image combinations may include a combination of an images produced with fluorescence imaging techniques with an image produced using one of laser speckle imaging techniques, laser doppler imaging techniques, reflectance imaging techniques and tissue oxygen related imaging techniques.

In some embodiments, the analysis module may be configured to analyze the acquired images by increasing a signal to noise ratio (SNR), removing ambient light background, linking images from multiple different channels, and acquiring information related to the acquired images at a specific detection depth.

In further embodiments, the acquired images may be obtained with fluorescence imaging techniques.

In still further embodiments, the target may be one of a fluorescence dye phantom, in vitro and in vivo tissue and an organ marked with fluorescence dye.

In some embodiments, the image visualization module may be further configured to provide a final improved image having reduced ambient light noise, a specific depth of detection, and combination of different multi-wavelength images obtained using different multi-wavelength imaging techniques.

In further embodiments, the at least one multi-wavelength illumination module may be configured to one of repeatedly illuminate the target in an on and off pattern using a single illumination pulse train; and repeatedly illuminate the target at different wavelengths in an on and off pattern using a multiple illumination control pulse train.

In still further embodiments, the multi-wavelength camera may be further configured to capture an original image ($Img_{sn}$) when illumination is present, wherein the captured original image contains illumination light and ambient noise light; and capture a background image ($Img_n$) when illumination is off, wherein the captured background image ($Img_n$) contains ambient light noise. The image visualization module may be configured to calculate an image that does not include the ambient light noise ($Img_s$ FIG. 3C) as follows:

$$Img_s = Img_{sn} - k \times Img_n$$

where $Img_{sn}$ is an original image, $Img_n$ is a background image and k is a function of exposure time $T_1$ and $T_2$.

BRIEF DESCRIPTION OF THE DRAWINGS

FIG. 2 is a diagram illustrating a pulse control of a single illumination source.

FIGS. 3A through 3C are fluorescence images illustrating removal of the background noise in accordance with some embodiments of the present inventive concept.

FIGS. 9A through 9F are images of in vitro imaging (porcine tissue) with room light (ambient light) off including NIR1, VIS, NIR2; color, overlay1, and overlay2, respectively, in accordance with some embodiments of the present inventive concept.

DETAILED DESCRIPTION

Figure 1:
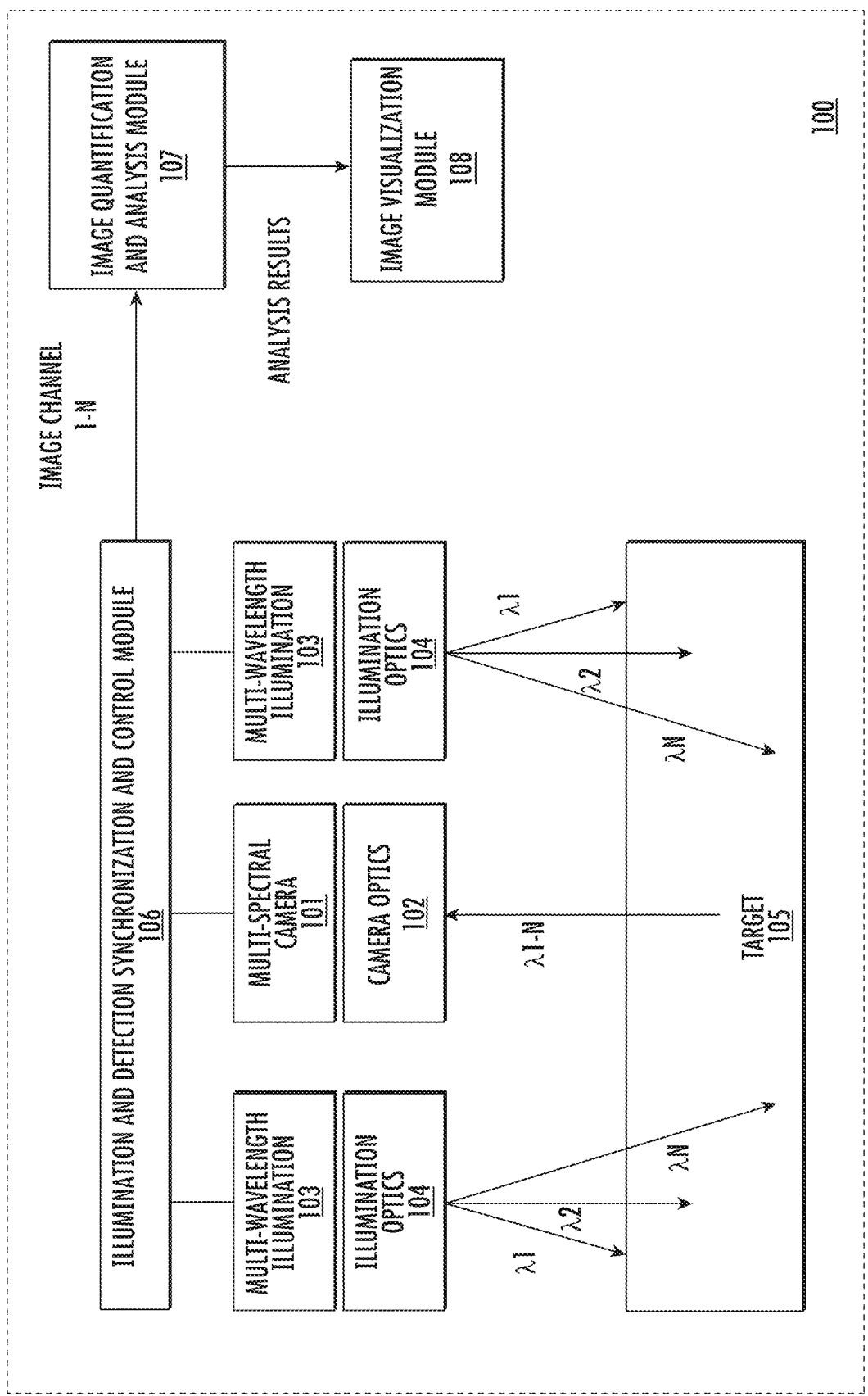
FIG. 1 is a block diagram illustrating a system/method for implementing multiple wavelength imaging in accordance with some embodiments of the present inventive concept.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed above, conventional near-infrared fluorescence devices generally provide this illumination from a single source. Use of high power illumination and optical filtering mechanisms may used to separate the fluorescence emission signal from excitation/ambient signal to increase signal to noise ratio. However, this design may not be satisfactory when the ambient light is present in the field of view (FOV). Thus, in practice, most of the current devices require that ambient light, such as the overhead room light, surgical light, head light and the like, to be turned off for imaging, which can be inconvenient or even disruptive during procedures. Furthermore, the depth of detection relative to the surface of tissues being imaged in current fluorescence technology design is not able to be determined and, therefore, may not be controllable. This is a result of the fact that current device designs generally either use a single wavelength laser that only allows a certain depth of penetration, or a broad band LED or Halogen illumination that leads to a heterogeneous, but un-definable depth of penetration.

Accordingly, some embodiments of the present inventive concept are based on multi-spectral imaging, pulsing illumination and synchronization between illumination and detection. Through a series of hardware designs and software modules, embodiments of the present inventive concept perform fluorescence imaging that, in contrast to existing fluorescence technologies, can reduce, or possibly eliminate, ambient light noise in the fluorescence imaging, achieve a specific depth of detection, and combine a fluorescence image together with other imaging technologies, such as laser speckle, laser doppler, reflectance imaging, tissue oxygen related imaging and the like in real-time in the same device. It will be understood that the multi-spectral imaging portion can be provided by a variety of solutions, including, for example, Multi-Spectral Physiologic Visualization (MSPV) as discussed, for example, in U.S. Pat. No. 10,390,718, the contents of which are incorporated herein by reference as if set forth in its entirety. Details with respect to embodiments of the present inventive concept will be discussed further with respect to FIGS. 1 through 10 below.

Referring first to FIG. 1, an imaging system 100 in accordance with some embodiments of the present inventive concept will be discussed. As illustrated in FIG. 1, the system 100 includes a multi-spectral camera 101; camera optics 102, for example, a lens, emission filter and the like; multi-wavelength illumination 103, for example, lasers, light emitting diodes (LEDs) and the like; illumination optics 104, for example, an excitation filter; an imaging target 105; an illumination and detection synchronization and control module 106; an image quantification and analysis module 107 and an image visualization module 108. The dotted line depicting system 100 in FIG. 1 includes all modules of the system 100. However, it will be understood that the modules may be part of the same device or in separate devices that communicate without departing from the scope of the present inventive concept.

As illustrated, λ1-N is the wavelength from channel 1 to channel N. The wavelengths may include any "N" wavelengths in the range of, for example, 400 nm to 1000 nm. For example, λ1 (~400 nm) to excite cascade blue, λ2 (~524 nm) to excite Eosin, λ3 (~624 nm) to excite daylight 633, λ4 (~780 nm) to excite indocyanine green. These dyes and wavelengths are provided as examples only and, therefore, should not limit the inventive concept.

As used herein, a "target" may be fluorescence dye phantom, in vitro and in vivo tissue, an organ marked with fluorescence dye and the like. These are provided as examples only and, therefore, embodiments of the present inventive concept are not limited thereto.

Illumination in accordance with embodiments of the present inventive concept is a multi-wavelength light source ranging from, for example, 400 nm visible light to 1000 nm near infrared (NIR) light. The wavelength characteristics of the illumination can be controlled using, for example, multiple lasers, LEDs or Halogens with front end optics, such as filters, to adjust the wavelength range. Some of the visible wavelength in the illumination is reflected directly from the surface of the target without any penetration and the near infrared wavelength will have different penetration levels usually within about 10 mm.

The camera system (101, 102, 103, 104) in accordance with embodiments discussed herein can detect illumination of multiple wavelengths and acquire an image through multiple imaging channels. The synchronization and control module 106 (control module) is configured to synchronize illumination and detection, so the camera can capture multiple wavelengths at the same time or one wavelength at a specific time.

The image qualification and analysis module 107 (analysis module) receives raw images over the image channel 1-N and is configured to apply predefined algorithms to the raw images to increase signal to noise ratio (SNR), remove ambient light background, link images of multiple channels, acquire information at a specific detection depth and the like.

The image visualization module 108 is configured receive analysis results and to perform multi-spectral image combinations, image enhancements, such as image fusion, contrast and brightness adjustment, overlay and the like and present the final results in real-time. As used herein, "real-time" refers to an amount of time so small that it appears to have occurred instantaneously. It will be understood that although not shown in FIG. 1, display (FIG. 10) is provided to view the images in real-time.

Referring now to FIG. 2, a single illumination pulse train will be discussed. The diagram of FIG. 2 illustrates synchronizing one pulsing illumination with camera exposure time in an on-off-on-off . . . repeating pattern to remove noise caused by ambient light in an imaging modality, such as fluorescence imaging.

It will be understood that many of the figures herein are illustrations of images obtained of the target region. However, all figures are presented herein in grey scale as colored drawings are not publishable in the patent process. Accordingly, some detail may be lost due to presentation in grey scale.

Referring to FIGS. 3A through 3C, images illustrating a background subtraction method using fluorescence imaging as an example in accordance with some embodiments of the present inventive concept will be discussed. FIG. 3A illustrates an image acquired while illumination is on (signal+noise); FIG. 3B illustrates an image acquired while illumination is off (noise); and FIG. 3C illustrates an image generated using the images of FIGS. 3A and 3B (signal). In other words, when illumination is on, an original image ($Img_{sn}$, FIG. 3A) is captured that contains a useful signal (illumination light)+noise (ambient light). When illumination is off, a background image ($Img_n$, FIG. 3B) is captured that contains noise (ambient light). The, the image illustrated in FIG. 3C is calculated and only contains useful signal ($Img_s$, FIG. 3C) as follows:

$$Img_s = Img_{sn} - k \times Img_n \qquad \text{Eqn. (1)}$$

where $Img_{sn}$ is an original image, $Img_n$ is a background image and k is a function of exposure time $T_1$ and $T_2$.

In these embodiments of the present inventive concept, this method may be combined with an image processing algorithm including image binning, normalization, sharpening and the like and may effectively increase image brightness, contrast and overall image quality.

Figure 4A:
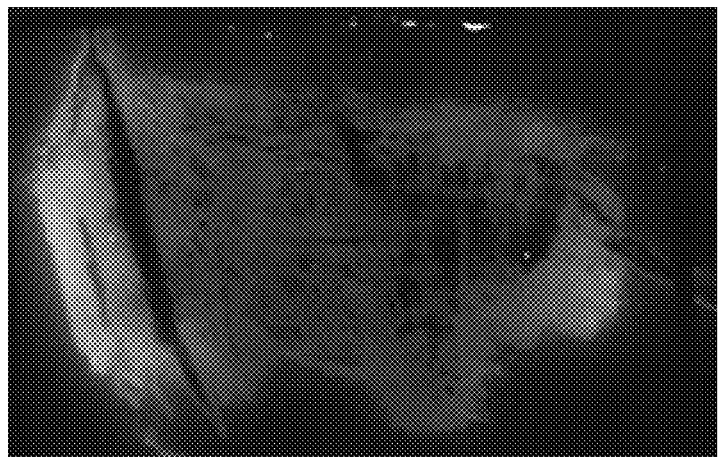
FIGS. 4A through 4C are fluorescence images illustrating removal of the background noise and comparing with fluorescence image without background noise in accordance with some embodiments of the present inventive concept.
Figure 4B:
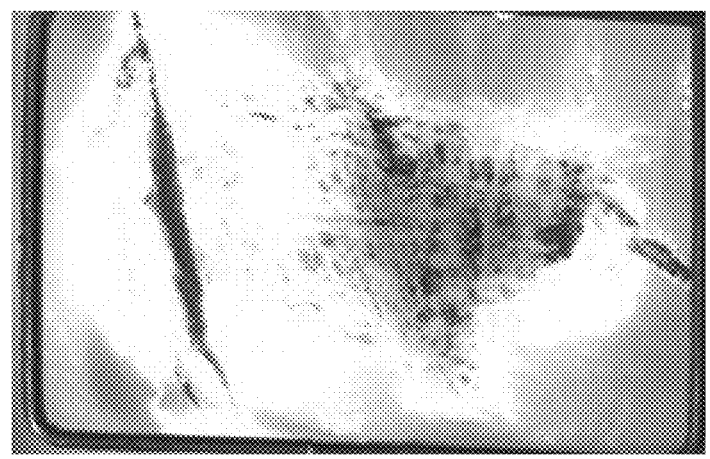
Figure 4C:

Referring now to FIGS. 4A through 4C, fluorescence images used for ambient light comparison with in vitro pig tissue as target will be discussed. FIG. 4A illustrates a fluorescence image obtained without ambient light; FIG. 4B illustrates a fluorescence image obtained with ambient light; and FIG. 4C illustrates a fluorescence image obtained with ambient light and using ambient light removal in accordance with embodiments of the present inventive concept discussed herein. As illustrated in FIGS. 4A through 4C, with the presence of ambient light (FIG. 4A) the quality of fluorescence image is reduced, compare FIG. 4A with FIG. 4B (no ambient light). However, after processing the image in FIG. 4B using methods and systems discussed herein discussed above with respect to FIGS. 1 through 3C, the fluorescence image without ambient light contamination is restored (FIG. 4C).

Figure 5:
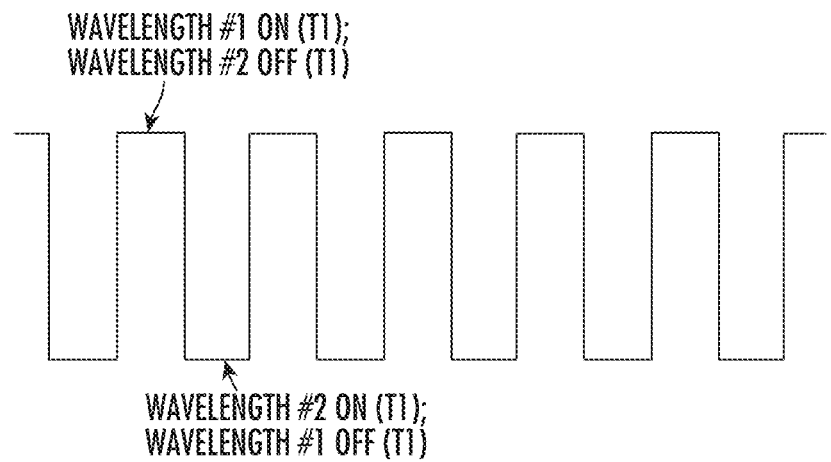
FIG. 5 is a diagram illustrating the pulse control of multiple illumination sources.

Referring now to FIG. 5, a multiple illumination control pulse train will be discussed. As illustrated, in some embodiments multiple pulsing sources may be synchronized at different wavelengths with camera exposure time in an (wavelength 1 on, wavelength 2 off)-(wavelength 2 on, wavelength 1 off) . . . repeating pattern to achieve multi-spectral and hyper-spectral fluorescence imaging using multiple dyes that are specific to different wavelengths. The dyes may be, for example, cascade blue, Eosin, Daylight 633, indocyanine green and the like without departing from the scope of the present inventive concept.

Figure 6:
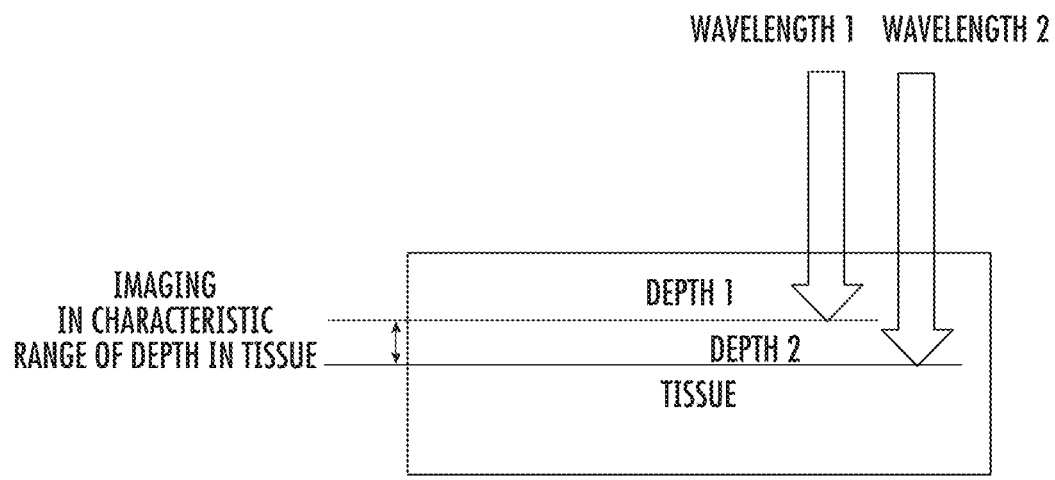
FIG. 6 is a block diagram illustrating systems achieving a specific range of detection depth in accordance with some embodiments of the present inventive concept.

Referring now to FIG. 6, a diagram illustrating an imaging a target at a certain range of characteristic detection depth in accordance with some embodiments of the present inventive concept will be discussed. In particular, multiple pulsing sources may be synchronized at different wavelengths with camera exposure time in an (wavelength 1 on, wavelength 2 off) at time T1-(wavelength 2 on, wavelength 1 off) at a time T2 . . . repeating pattern to achieve fluorescence imaging in a characteristic range of tissue depths using one fluorophore that is responsive to multiple wavelengths or multiple fluorophore responsive to two multiple wavelengths. As illustrated in FIG. 6, the various wavelengths penetrate the target at different depths, for example, depth 1 and depth 2.

Figures 7A, 7B, 7C:
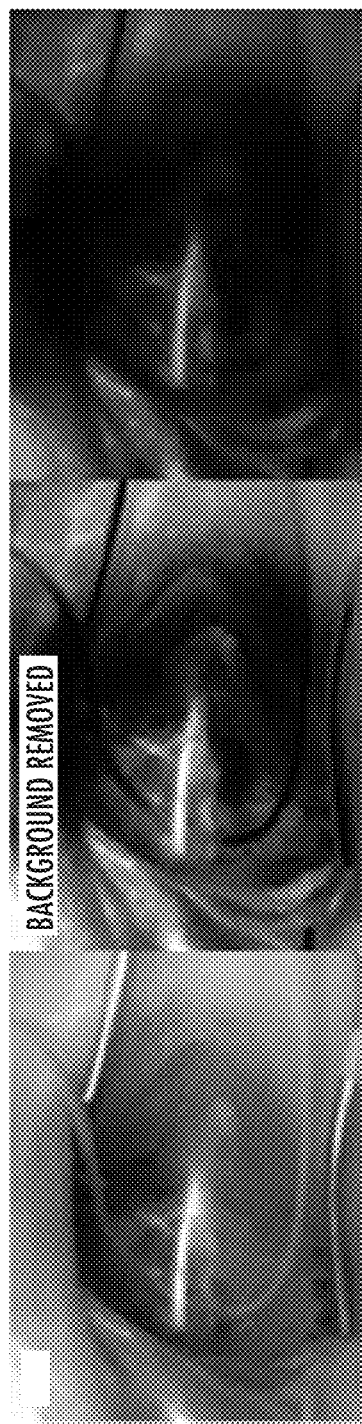
FIGS. 7A through 7D are images illustrating a composite of embodiments of the inventive concept and a commercial fluorescence technology (SPY from Novadaq Technologies, Inc.) imaging the same femoral artery and surrounding tissue in a porcine model in sequential fashion separated by five minutes (SPY $1^{st}$, then the inventive concept. 0.5 cc of standard dilution of ICG dye for each imaging acquisition was injected).
Figure 7D:

Referring to FIGS. 7A through 7D, images obtained using embodiments discussed herein in an in vivo porcine model of the femoral artery, using single wavelength pulsed excitation illumination will be discussed. FIG. 7A is a raw image; FIG. 7B is an image with the background removed; FIG. 7C is an image including visualization with fluorescence color scheme; and FIG. 7D is predicate device imaging. FIGS. 7A through 7D documents certain embodiments of the inventive concept in porcine tissue, using a single wavelength (excitation) pulsed illumination. The femoral artery and surrounding tissue are visualized by the injection of 0.5 cc of diluted ICG dye, using (a) the raw imaging data from the inventive concept in certain embodiments; (b) the imaging data with the background removed; and (c) the same FOV imaged with the Novadaq Technologies SPY near-infrared fluorescence device (single wavelength). These images are provided for example only and, therefore, do not limit embodiments of the present inventive concept.

Some embodiments of the present inventive concept may be applied in sequential combination with different imaging modalities, such as laser speckle, laser doppler, reflectance imaging, tissue oxygen related imaging and the like without departing from the scope of the present inventive concept.

In some embodiments of the present inventive concept one pulsing illumination is synchronized with camera exposure time in an on-off-on-off . . . repeating pattern to remove background noise caused by ambient light in an imaging modality, such as fluorescence imaging. In these embodiments, one dye and one wavelength may be used to remove noise.

In some embodiments of the present inventive concept, multiple pulsing sources may be synchronized at different wavelengths with camera exposure time in an (wavelength 1 on, wavelength 2 off)-(wavelength 2 on, wavelength 1 off) . . . repeating pattern to remove noise caused by residue of dye in an imaging modality such as fluorescence imaging. In these embodiments, one dye and multiple wavelengths may be used to remove noise.

In some embodiments, multiple pulsing sources may be synchronized at different wavelengths with camera exposure time in an (wavelength 1 on, wavelength 2 off)-(wavelength 2 on, wavelength 1 off) . . . repeating pattern to achieve fluorescence imaging in a characteristic range of tissue depth using one dye that is responsive to multiple wavelengths. In these embodiments, one dye and multiple wavelengths may be used to reveal a specific depth.

In some embodiments, multiple pulsing sources may be synchronized at different wavelengths with camera exposure time in an (wavelength 1 on, wavelength 2 off)-(wavelength 2 on, wavelength 1 off) . . . repeating pattern to achieve fluorescence imaging in a characteristic range of tissue depth using multiple dyes that are responsive to multiple wavelengths. In these embodiments, multiple dyes and multiple wavelengths may be used to reveal a specific depth.

In some embodiments, multiple pulsing sources may be synchronized at different wavelength with camera exposure time in an (wavelength 1 on, wavelength 2 off)-(wavelength 2 on, wavelength 1 off) . . . repeating pattern to achieve multi-spectral and hyper-spectral fluorescence imaging using multiple dyes that are specific to different wavelengths. In these embodiments, multiple dyes and multiple wavelengths may be used to do multiple fluorescence at the same time.

Figures 8A, 8B, 8C:
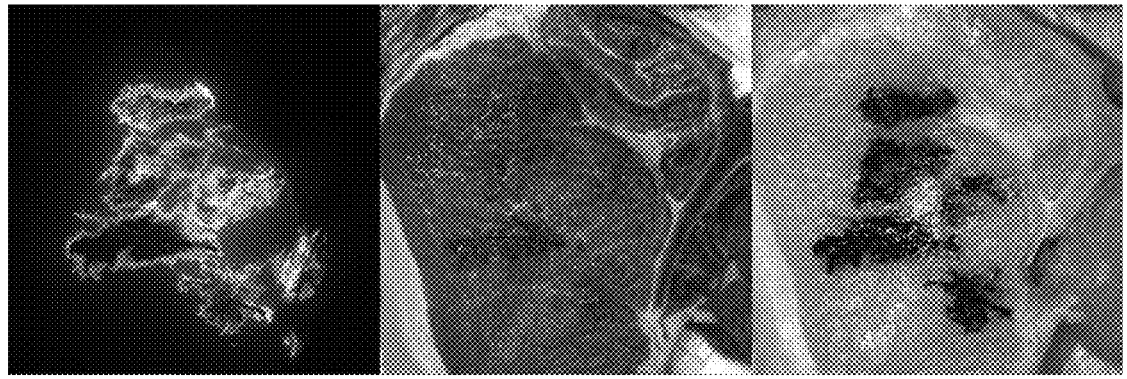
FIGS. 8A through 8F are images of in vitro imaging (porcine tissue) with room light on including NIR1, VIS, NIR2; color, overlay1 and overlay2, respectively, in accordance with some embodiments of the present inventive concept.

Referring now to FIGS. 8A through 8F, multispectral raw images acquired in synchronization and real time will be discussed. To effectively illustrate these points for both imaging modalities (laser speckle and NIRF) at the same time, ex vivo in vitro imaging is used. In FIGS. 8A-8F, this in vitro imaging (porcine tissue) is performed with room light on and specifically illustrates NIR1, VIS, NIR2; color, overlay1, overlay2, respectively, as will be discussed in further detail below. In particular, FIG. 8A illustrates an image acquired using a near infrared channel 1 (>815 nm) for fluorescence imaging ($Img_{NIR1}$); FIG. 8B is an image acquired using a visible channel (<700 nm) for reflectance imaging ($Img_{VIS}$); and FIG. 8C is an imaged acquire using a near infrared channel 2 (700 nm-815 nm) for reflectance, laser speckle, laser doppler imaging ($Img_{NIR2}$).

Figures 8D, 8E, 8F:
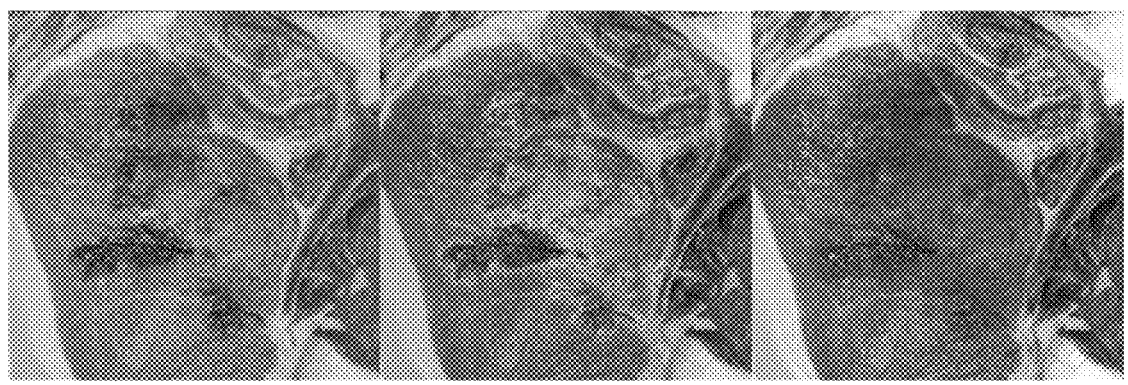

These images may be analyzed and displayed and saved (multispectral overlay images) in real time as discussed with respect FIGS. 8D through 8E. FIG. 8D illustrates a color view for anatomical imaging (show in grey scale). FIG. 8E illustrates fluorescence image overlays on visible image (colormap 1: blue→green→yellow→red color scheme) (shown in grey → scale); and FIG. 8F illustrates fluorescence image overlays on visible image (colormap 2: green intensity color scheme).

The overlay may be defined as follow: background layer: $Img_{VIS}(i,j)$ is the visible image with brightness, contrast and gamma value adjustment; foreground layer: $RGB_{ICG}(i,j)$ is the ICG image ($Img_{NIR1}$) that is converted into a red green blue (RGB) color schedule based on a predefined color map and wherein a transparency factor ($T(i, j)$) is defined as $$T(i, j) = \left( \frac{Img_{NIR_1}(i, j) - \text{Min}(Img_{NIR_1}(i, j))}{\text{Max}(Img_{NIR_1}(i, j)) - \text{Min}(Img_{NIR_1}(i, j))} \right)^x \qquad \text{Eqn. (2)}$$

where x is a normalization parameter between 0 and 1; and i and j represent the index of the horizontal and vertical pixels.

FIGS. 9A through 9F are images of in vitro imaging (porcine tissue) with room light (ambient light) off and, specifically, NIR1, VIS, NIR2; color, overlay1, and overlay2, respectively, in accordance with some embodiments of the present inventive concept. Again, to effectively illustrate these points for both imaging modalities (laser speckle and NIRF) at the same time, ex vivo in vitro imaging is used. Comparing FIGS. 8A through 8F (room light on) and FIGS. 9A through 9F (room light off), methods and systems in accordance with embodiments of the present inventive concept clearly provide an image having reduced ambient light noise and an enhanced ICG fluorescence signal.

To summarize FIGS. 8A through 9F, FIGS. 8A-F and 9A-F look substantially similar due to the fact that since the images in FIGS. 9A-F are shown after the ambient light removal based on methods discussed herein in accordance with some embodiments of the present inventive concept. Ultimately, the goal is to make the final images the same (no ambient light vs. ambient light after removal). Although not shown, the original images are different before removal.

Figure 10:
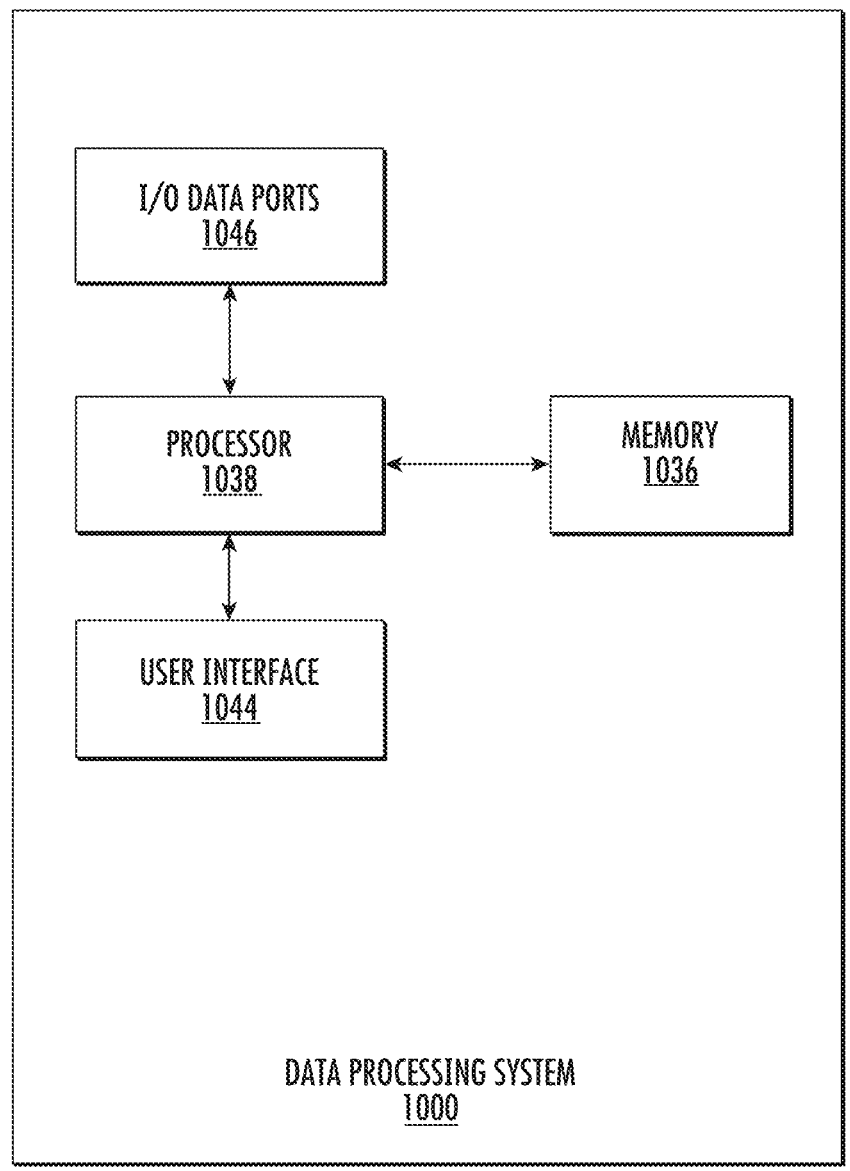
FIG. 10 is a block diagram of a data processing system that may be used in accordance with some embodiments of the present inventive concept.

As discussed above, some embodiments of the present inventive concept process images to calculated new images. These embodiments generally use a data processor. Referring now to FIG. 10, an example embodiment of a data processing system 1000 suitable for use in accordance with some embodiments of the present inventive concept will be discussed. For example, the data processing system 1000 may be provided anywhere in the system without departing from the scope of the present inventive concept. As illustrated in FIG. 10, the data processing system 1000 includes a user interface 1044 such as a display, a keyboard, keypad, touchpad or the like, I/O data ports 1046 and a memory 1036 that communicates with a processor 1038. The I/O data ports 1046 can be used to transfer information between the data processing system 1000 and another computer system or a network. These components may be conventional components, such as those used in many conventional data processing systems, which may be configured to operate as described herein. This data processing system 1000 may be included in any type of computing device without departing from the scope of the present inventive concept.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), microcontroller or graphics processing unit.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed example embodiments of the inventive concept. Although specific terms are employed, they are used in a generic and descriptive sense only and not for purposes of limitation, the scope of the inventive concept being defined by the following claims.

What is claimed is:

1. A system for obtaining an image of a target, the system comprising:
   at least one multi-wavelength illumination module configured to illuminate a target using two or more different wavelengths, each of the two or more different wavelengths penetrating the target at different depths;
   wherein at least one of the two or more different wavelengths is a fluorescence excitation wavelength or range of wavelengths that switch on and/or off responsive to pulse train triggering signals; and wherein the remaining ones of the two more wavelengths are visible wavelengths for simultaneous scattering or reflection imaging;

a multi-wavelength camera configured to detect the two or more scattered and fluorescence light intensities of different wavelengths from an illuminated target on corresponding different channels and acquire corresponding images of the target based on the detected light intensities of two or more different wavelengths illuminating the target;

a control module configured synchronize illumination of the target by the at least one multi-wavelength illumination module and detection of the scattered and fluorescence light intensities of two or more different wavelengths from the target when illumination is present and intensity of ambient noise light when illumination is off by the camera;

an analysis module configured to receive the acquired images of the target associated with each of the two or more wavelengths and analyze the acquired images to provide analysis results on a scaling relation among different light intensities; and an image visualization module configured to receive the analysis results and modify the acquired images based on the analysis results to provide a final improved image in real-time, the final improved images having reduced intensity of ambient noise light by an intensity scaling relation.

2. The system of claim 1, wherein the image visualization module is configured to modify the image by performing multi-spectral image combinations, image enhancements, contrast and brightness adjustment, noise reduction and overlay procedures to provide the final improved image in real-time.

3. The system of claim 2, wherein multi-spectral image combinations comprise a combination of images produced with fluorescence imaging techniques with an image produced using one of laser speckle imaging techniques, laser doppler imaging techniques and reflectance imaging techniques.

4. The system of claim 1, wherein the analysis module is configured to analyze the acquired images by increasing a signal to noise ratio (SNR), reducing ambient noise light intensity by an intensity scaling relation, linking images from multiple different channels under different illumination conditions, cancer tracing and tumor marking fluorescence techniques and acquiring information related to the acquired images at a specific detection depth.

5. The system of claim 1, wherein the acquired images are processed obtained with fluorescence imaging techniques and processed to obtain a final improved image having reduced intensity of ambient noise light by an intensity scaling relation.

6. The system of claim 1, wherein the image visualization module is further configured to provide a final improved image having reduced ambient noise light intensity by an intensity scaling relation, a range of depth of detection, and combination of different multi-wavelength images obtained using different multi-wavelength imaging techniques.

7. The system of claim 1, wherein at least one multi-wavelength illumination module is configured to one of:

repeatedly illuminate the target in an on and off pattern using a single control pulse train; and repeatedly illuminate the target at different wavelengths in an on and off pattern using a single control pulse train.

8. The system of claim 1:

wherein the multi-wavelength camera is further configured to capture an original image ($Img_{sn}$) that records the intensities of scattered light and fluorescent light from a target when illumination is present during a time period of $T_1$, wherein the captured original image contains spatial distribution of the scattered and fluorescent light intensity on the target surface and ambient noise light intensity; and capture a background image ($Img_n$) on the target when illumination is off during a time period of $T_2$, wherein the captured background image ($Img_n$) records intensity of ambient noise light only; and wherein the image visualization module is configured to calculate an image that reduce the intensity of ambient noise light ($Img_s$) as follows:

$$Img_s = Img_{sn} - k \times Img_n$$

where $Img_{sn}$ is an original image, $Img_n$, is a background image and k is a function of time periods of $T_1$ and $T_2$.

9. A method for obtaining an image of a target, the method comprising:

illuminating a target using two or more different wavelengths, each of the two or more different wavelengths penetrating the target at different depths;

wherein a plurality of the two or more different wavelengths are fluorescence excitation wavelengths or ranges of wavelengths, each of the plurality of the two or more different wavelengths being individually switched on in sequence and then off responsive to pulse train triggering signals; and wherein the remaining ones of the two more different wavelengths are visible wavelengths for simultaneous scattering or reflection imaging;

detecting the intensities of scattered light and fluorescent light of two or more different wavelengths from the illuminated target on corresponding different channels;

acquiring corresponding images of the target based on the detected light intensities of two or more different wavelengths from the illuminated target;

synchronizing illumination of the target by the at least one multi-wavelength illumination module and detection of the target by light intensities of the two or more different wavelengths by the camera at conditions when one fluorescence excitation illumination is present while others are off and a different fluorescence excitation illumination is present while others are off;

receiving the acquired images of the target associated with each of the two or more wavelengths and analyzing the acquired images to provide analysis results on an intensity scaling relation among different light intensities; and receiving the analysis results and modifying the acquired images based on the analysis results to provide a final improved image in real-time, the final improved images having reduced a specific depth of penetration of the fluorescence image;

wherein at least one of the illuminating, detecting, acquiring, synchronizing, receiving, analyzing, receiving and modifying are performed by at least one processor.

10. The method of claim 9, further comprising modifying the image by performing multi-spectral image combinations, image enhancements, contrast and brightness adjustment, noise reduction by an intensity scaling relation and overlay procedures to provide the final improved image in real-time.

11. The method of claim 10, wherein combining multi-spectral images comprises combining an images produced with fluorescence imaging techniques with an image produced using one of laser speckle imaging techniques, cancer tracing and tumor marking fluorescence imaging techniques, laser doppler imaging techniques and reflectance imaging techniques.

12. The method of claim 9, further comprising analyzing the acquired images by increasing a signal to noise ratio (SNR), reducing ambient noise light intensity by an intensity scaling relation, linking images from multiple different channels under different illumination conditions, and acquiring information related to the acquired images at a specific detection depth.

13. The method of claim 9, wherein acquiring images comprises acquiring images using fluorescence imaging techniques.

14. The method of claim 9, further comprising providing a final improved image having reduced intensity of ambient noise light by an intensity scaling relation, a specific depth of detection, and combination of different multi-wavelength images obtained using different multi-wavelength imaging techniques.

15. The method of claim 9, further comprising:
one of repeatedly illuminating the target in an on and off pattern using a single control pulse train; and
repeatedly illuminating the target at different wavelengths in an on and off pattern using a single control pulse train.

16. The method of claim 9, further comprising:
capturing a first fluorescence image ($Img_{sn}$) when one of the fluorescence excitation illumination is present during a time period of $T_1$, wherein the captured image contains light intensity from a range of depth of penetration (depth 2);
capturing a second fluorescence image ($Img_n$) when a different fluorescence excitation illumination is present during a time period of $T_2$, wherein the captured image contains light intensity from a different range of depth of penetration (depth 1); and
calculating a fluorescence image of specific depth of penetration as follows:

$$Img_s = Img_{sn} - k \times Img_n$$

where $Img_{sn}$ is a fluorescence image with deeper penetration, $Img_n$ is another fluorescence image with a shallower penetration and k is a function of exposure time $T_1$ and $T_2$ and dye sensitivity ratio.

17. A computer program product for obtaining an image of a target, the computer program product comprising:
a non-transitory computer-readable storage medium having computer-readable program code embodied in the medium, the computer-readable program code comprising:
computer readable program code for illuminating a target using two or more different wavelengths, each of the two or more different wavelengths penetrating the target at different depths;
wherein at least one of the two or more different wavelengths is a fluorescence excitation wavelength or range of wavelengths that switch on and/or off responsive to pulse train triggering signals; and
wherein the remaining ones of the two more wavelengths are visible wavelengths for simultaneous scattering or reflection imaging;
computer readable program code for detecting the scattered and fluorescent light intensities of two or more different wavelengths from the illuminated target on corresponding different channels;
computer readable program code for acquiring corresponding images of the target with two or more different wavelengths illuminating the target;
computer readable program code for synchronizing illumination of the target by the at least one multi-wavelength illumination module and detection of the scattered and fluorescent light intensities of two or more different wavelengths by the camera;
computer readable program code for receiving the acquired images of the target associated with each of the two or more wavelengths when the illumination is present and of the target when the illumination is off and analyzing the acquired images to provide analysis results on a scaling relation among different light intensities; and
computer readable program code for receiving the analysis results and modifying the acquired images based on the analysis results to provide a final improved image in real-time, the final improved images having reduced intensity of ambient noise light.

18. The computer program product of claim 17, further comprising:
computer readable program code for capturing an original image ($Img_{sn}$) that records the light intensity of scattering by and fluorescence from a target under illumination during a time period of $T_1$, wherein the captured original image contains spatial distribution of the scattered and fluorescent light intensity on the target surface and ambient noise light intensity;
computer readable program code for capturing a background image ($Img_n$) when illumination is off during a time period of $T_2$, wherein the captured background image ($Img_n$) contains ambient noise light intensity only; and
computer readable program code for calculating an image that does not include the ambient noise light intensity ($Img_s$) as follows:

$$Img_s = Img_{sn} - k \times Img_n$$

where $Img_{sn}$ is an original image, $Img_n$ is a background image and k is a function of time periods of $T_1$ and $T_2$.

* * * * *